United States Patent [19]

Doi et al.

[11] Patent Number: 4,812,579

[45] Date of Patent: Mar. 14, 1989

[54] PROCESS FOR PRODUCING N-SUBSTITUTED MALEIMIDES

[75] Inventors: Shunichi Doi; Yasuyuki Takayanagi, both of Yokohama, Japan

[73] Assignee: Nitto Chemical Industry Co., Ltd., Tokyo, Japan

[21] Appl. No.: 107,478

[22] Filed: Oct. 13, 1987

Related U.S. Application Data

[63] Continuation of Ser. No. 778,709, Sep. 23, 1985.

[30] Foreign Application Priority Data

Oct. 3, 1984 [JP] Japan ................................ 59-206199

[51] Int. Cl.$^4$ ............... C07D 207/448; C07D 207/452
[52] U.S. Cl. ....................................... 548/548; 548/549
[58] Field of Search .................................. 548/548, 549

[56] References Cited

U.S. PATENT DOCUMENTS 3,338,919  8/1967  Nield ................................... 548/548

FOREIGN PATENT DOCUMENTS 906494   8/1972  Canada.
1041027  9/1966  United Kingdom.

OTHER PUBLICATIONS

J. Org. Chem., 24, 135-136 (1959) (Coleman et al.).
Org. Syth., vol. 5, 944-946 (1973).
Calmon et al. (Ed), Ion Exchangers in Organic and Biochemistry, Interscience, NY, NY (1957), pp. 658, 659 and 663-667.

Primary Examiner—David B. Springer
Attorney, Agent, or Firm—Cushman, Darby & Cushman

[57] ABSTRACT

A process for producing N-substituted maleimides which comprises heating maleic anhydride and an aromatic or aliphatic amine, or maleic acid monoamides obtained from them, in the presence of an ion exchange resin in an organic solvent to effect cyclodehydration.

14 Claims, No Drawings

PROCESS FOR PRODUCING N-SUBSTITUTED MALEIMIDES

This is a continuation of application Ser. No. 778,709, filed Sept. 23, 1985.

BACKGROUND OF THE INVENTION

1. Field of the Invention

This invention relates to a process for producing N-substituted maleimides. More particularly, it relates to a process for producing N-substituted maleimides by heating maleic anhydride and an aromatic or aliphatic amine, or maleic acid monoamides obtained from them, in an organic solvent in the presence of a catalyst.

N-Substituted maleimides are compounds which can be used in a very wide field of applications as raw materials or intermediates for pharmaceuticals, agricultural chemicals, dyes and high molecular substances.

2. Description of the Prior Art

Various processes for producing N-substituted maleimides have hitherto been known.

For example, there is known a method which comprises obtaining N-substituted maleimides by heating at 180° C. maleic acid monoamides (maleamic acids), which are easily obtainable from maleic anhydride and amines such as butylamine, octylamine, decylamine and dodecylamine, to effect cyclodehydration. (L. E. Coleman et al., J. Org. Chem., 24, 135 (1959)). However, this method cannot be used in practice since it gives a low yield of intended products of only 15 to 50% and moreover yields a large amount of polymers of a polyimide structure as a by-product.

A well known laboratory method of preparation is to treat maleic anhydride and aniline in the presence of sodium acetate catalyst using a dehydrating agent such as acetic anhydride. (Org. Synth. Coll. Vol. 5, 944 (1973)). Though the method can give N-substituted maleimides in a relatively high yield (75 to 80%), it has a defect of high production cost since it requires the use of a stoichiometric amount of acetic anhydride, which results in additional cost of the auxiliary material, and thus it is unsuitable for industrial production.

On the other hand, a conceivably advantageous process for industrial production is to effect the cyclodehydration of maleic acid monoamides under milder conditions using an effective dehydration catalyst without using dehydrating agents.

Various attempts have been made also regarding to such a process. There have been proposed, for example, a method which uses a basic catalyst such as an alkali metal acetate, sodium hydroxide or triethylamine as a catalyst (Japanese Patent Application publication No. 24024/1972, corresponding to Canad. Pat. No. 906494 and West Germany Pat. No. 2100800) and a method which uses an acidic catalyst such as sulfuric acid and a sulfonic acid (Brit. Pat. Specification No. 1041027).

However, these methods using such catalysts are not yet fully satisfactory in suppressing side reactions since they give polymeric products as a by-product. Moreover, they require complicated steps in the separation and recovery of the catalyst and the removal of by-products from the reaction products and thus cannot be said to be an advantageous process for industrial production.

As described above, the prior art cyclodehydration of maleic acid monoamides in the presence of a catalyst gives relatively a large amount of side reaction products including polymeric by-products and consequently has drawbacks in yield, product purity and operation procedures. Thus, the suppression of side reactions including polymer formation has become an important problem to be solved.

SUMMARY OF THE INVENTION

This invention has been completed to solve the problems of prior methods. Thus, one object of this invention is to provide a process for producing N-substituted maleimides in an industrially advantageous way. Further object of this invention is to provide a process for producing N-substituted maleimides which can give N-substituted maleimides in a high yield while suppressing side reactions including polymer formation.

The present inventors have made extensive studies to achieve the above-mentioned objects. As a result, it has been found that when maleic anhydride and amines, or maleic acid monoamides obtained from them, are heated in an organic solvent by using an ion exchange resin, a very common substance, as a catalyst to effect cyclodehydration, N-substituted maleimides can be obtained in a high yield without formation of polymeric by-products, and the separation of the catalyst from the reaction product can be operated very easily, and further that when the above reaction is conducted by using as the solvent an admixture of an aromatic hydrocarbon solvent and an aprotic polar solvent the results of the reaction is further improved. This invention has been accomplished on the basis of above findings.

The gist of this invention is as follows. One method of this invention is a process for producing N-substituteds maleimide which comprises heating maleic anhydride and an aromatic or aliphatic primary amine in the presence of an ion exchange resin in an organic solvent in the temperature range of 50° C. to 160° C. to effect cyclodehydration.

Another method of this invention is a process for producing N-substituted maleimides which comprises reacting maleic anhydride and an aromatic or aliphatic primary amine to form maleic acid monoamides, with or without separating the maleic acid monoamides from the reaction mixture, and heating the maleic acid monoamides in the presence of an ion exchange resin in an organic solvent in the temperature range of 50° C. to 160° C. to effect cyclodehydration.

DESCRIPTION OF THE PREFERRED EMBODIMENTS

Some embodiments of this invention will be elucidated below.

Maleic anhydride, a starting material for this invention, may be of any source and is conveniently used after properly selected from commercially available maleic anhydride. Maleic anhydride is usually produced by the oxidation of benzene, n-butene or n-butane. Though the reaction proceeds in a similar manner also when maleic acid is used in place of maleic anhydride, the use of the former is disadvantageous from the viewpoint of reactivity and economical efficiency.

Examples of aromatic primary amines, another starting material for this invention, include aniline, naphthylamine, toluidine, dimethylaniline, chloroaniline, dichloroaniline, hydroxyaniline, nitroaniline, and phenylenediamine, preferred among these being aniline, toluidine, chloroaniline, dichloroaniline, hydroxyaniline and nitroaniline. Examples of aliphatic primary amines include methylamine, ethylamine, propylamine, butylamine, benzylamine, cyclohexylamine and ethylenediamine, preferred among these being methylamine, butylamine and cyclohexylamine. The aromatic or aliphatic primary amines are preferably used in the range of 0.8 to 1.2 mole relative to 1 mole of maleic anhydride.

The cyclodehydration of this invention is carried out in an organic solvent in the presence of an ion exchange resin used as a catalyst.

The first method of this invention comprises heating maleic anhydride and an above-mentioned aromatic or aliphatic primary amine in the presence of an ion exchange resin in an organic solvent in the temperature range of 50° C. to 160° C. Although the reaction can be carried out in various optional ways, a preferred method from the viewpoint of operational procedures and other factors is one which comprises placing maleic anhydride, a primary amine, an organic solvent, and an ion exchange resin into a reactor each in a predetermined amount and then heating them up to a given temperature to effect reaction, or one which comprises placing maleic anhydride, an organic solvent, and an ion exchange resin each in a predetermined amount into a reactor, heating them to a given temperature, and then adding gradually a primary amine thereto.

The organic solvent used in this invention may be any one so long as it can dissolve maleic anhydride, aromatic or aliphatic primary amines, and maleic acid monoamides, and does not react with ion exchange resins. Preferred solvents are aromatic hydrocarbon solvents such as benzene, toluene, xylene, ethylbenzene, styrene and cumene. Particularly preferred are benzene, toluene and xylene.

The amount of the organic solvent to be used is not restricted specifically but, from operational and economical considerations, it is preferably used in such an amount as to give a concentration of the products of about 10 to 50%, particularly preferably about 15 to 35%. Further, when a mixture of the above-mentioned aromatic hydrocarbon solvent with an aprotic polar solvent is used as the organic solvent, the reaction can be further promoted. Examples of aprotic polar solvents used include formamide, N-methylformamide, dimethylformamide, dimethylacetamide, dimethyl sulfoxide, sulfolane and hexamethylphosphotriamide. Preferred among these are dimethylformamide, dimethylacetamide and dimethyl sulfoxide.

Though the aprotic polar solvent can be used in any desired amount, it is preferably used in an amount of 50% or less, preferably about 2 to 30%, based on the total amount of solvent.

As illustrative examples of ion exchange resins used as a catalyst in this invention, any of strongly acidic, weakly acidic, strongly basic and weakly basic ion exchange resins of gel or macroporus type can be given. From the consideration of the activity and the thermal stability of the resin, strongly acidic, weakly acidic, or weakly basic ion exchange resins are preferable. Strongly acidic ones are particularily preferable and their macroporous typed ones are more particularily preferable. Preferred examples of strongly acidic ion exchange resins are those formed of polymers having sulfonic acid groups and those formed of fluorocarbon polymers having carboxyl groups. Normally, strongly acidic ion exchange resins are preferably used including those obtained by copolymerizing styrene with a crosslinkable monomer such as divinylbenzene and then sulfonating the resulting resin or resins obtained by the condensation of phenolsulfonic acid with formaldehyde and having a gel-like or a macroporous structure. As illustrative examples of crosslinked polystyrene sulfonic acid ion exchange resins, there are macroporous typed one and gel typed ones: The former includes Amberlite® 200C (Rohm & Haas, USA), Amberlyst® 15 (Rohm & Haas, USA), Dowex® MSC-1 (Dow Chemical, USA), Diaion® RCP-150H (Mitsubishi Chemical Ind. Co., Japan), Diaion® HPK-55 (Mitsubishi Chemical Ind. Co., Japan), Lewatit® SP-120 (Bayer A.G., West Germany) and Duolite® C-26 (Duolite International, France); and the latter includes Amberlite® IR-120B (Rohm & Haas, USA), Dowex® 50WX8 (Dow Chemical, USA), Diaion® SK1B (Mitsubishi Chemical Ind. Co., Japan), Diaion® PK 216 (Mitsubishi Chemical Ind. Co., Japan), Lewatit® S 100 (Bayer A.G., West Germany), Duolite® C-20 (Duolite International, France) and the like. Preferred among these are Amberlyst® 15, Amberlite® 200C, Amberlite® IR-120B, Dowex® 50WX8, Diaion® RCP-150H, Diaion® HPK-55 and Duolite® C-26.

Preferred weakly acidic ion exchange resins to be used are those formed of polymers having carboxyl groups or phosphonic acid groups. These resins are usually prepared by hydrolyzing copolymers of a methacrylic or acrylic ester with divinylbenzene. As illustrative examples of crosslinked poly(meth)acrylate ion exchange resin of gel type there are Amberlite® IRC 50 (Rohm & Haas, USA) and Dowex® CCR-2 (Dow Chemical, USA).

Preferred strongly basic ion exchange resins are those formed of polymers having quaternary ammonium groups. These resins are usually prepared by subjecting a copolymer of styrene with divinylbenzene to chloromethylation followed by quaternization using a tertiary amine. As illustrative examples of crosslinked quarternary ammonium salt ion exchanges (OH-type), Amberlyst® A-26 (Rohm & Haas, USA) as a representative of macroporous typed ones and Amberlite® IRA-400 (Rohm and Haas, USA) as a representative of gel typed ones can be given.

Preferred weakly basic ion exchange resins to be used are those formed of polymers having tertiary or lower order amino groups. These resins are usually prepared by subjecting a copolymer of styrene with divinylbenzene to chloromethylation followed by amination using a secondary amine or by subjecting a copolymer of a (meth)acrylic ester with divinylbenzene to a reaction with a polyamine such as N,N-dimethylaminopropylamine. As illustrative examples of crosslinked tertiary amine ion exchanges, Amberlyst® A-21 (Rohm & Haas, USA) or Dowex® MWA-1 (Dow Chemical, USA) as a representative of macroporous typed ones and Amberlite® IR-45 (Rohm & Haas, USA) as a representative of gel type ones can be given.

The amount of ion exchange resins to be used is not specifically limited but is usually in the range of 1 to 40% by weight, preferably 2 to 25% by weight, based on the amount of the reaction liquid.

The reaction temperature is selected in the range of 50° C. to 160° C., preferably 70° C. to 140° C., from the viewpoint of the activity and the thermal stability of ion exchange resins used as a catalyst.

There is no particular limitation as to the reaction pressure. A wide range of pressure may be adopted including normal, superatmospheric, and reduced pressures.

The reaction time varies depending upon such conditions as the concentration of starting materials, the amount of catalyst, the solvent, and the reaction temperature. Usually a reaction time of about 0.5 hour to 24 hours is suitable.

The N-substituted maleimide thus formed can be easily isolated and collected by separating the ion exchange resin from the reaction mixture by filtration and then distilling off the solvent from the filtrate. When a further purification is necessary, distillation, recrystallization, and the like can be conducted in a conventional manner.

The ion exchange resin used as the catalyst in the process of this invention can be reused repeatedly, and can be treated for maintenance of catalytic activity or regeneration. A preferable such treatment is washing with a dilute acid or an organic solvent for acid-type ion exchange resins and washing with a dilute alkali or an organic solvent for base-type ion exchange resins.

The second method of this invention comprises reacting maleic anhydride with an aromatic or aliphatic primary amine in the absence of ion exchange resins and then subjecting the maleic acid monoamides thus formed to cyclodehydration in the presence of an ion exchange resin. The cyclodehydration step is conducted in the same manner as in the first method mentioned before. In the reaction step, the maleic acid monoamides formed may be subjected to cyclodehydration also without being isolated from the reaction mixture. It is of course possible to use as the starting material maleic acid monoamides formed separately by the above-mentioned reaction of maleic anhydride with amines.

The synthesis of maleic acid monoamides is preferably carried out in an organic solvent. The organic solvents used are aromatic hydrocarbon solvents or mixtures thereof with aprotic polar solvents mentioned above. The reaction proceeds easily at a reaction temperature of about 150° C. or lower with no catalyst used particularly. The reaction temperature is suitably from room temperature to 100° C. The reaction time varies depending on the reaction temperature and the solvent used but is suitably in the range of 0.5 hour to 24 hours.

According to the process of this invention, N-substituted maleimides can be obtained in a high yield with no polymeric by-product being formed. Moreover, this invention has following advantages.

(i) Since no polymeric side-reaction product is formed, markedly easier operations are possible in production steps.

(ii) Since the amount of by-products is small, the purification of the product can be easily conducted.

(iii) The yield of the intended product is high.

(iv) The separation of the catalyst from the reaction product is extremely easy.

(v) The catalyst can be reused.

(vi) When aprotic solvents are used in the form of an admixture with the organic solvent, the reaction temperature can be lowered and the reaction time can be shortened.

Thus, the process of this invention is not only a novel process not described in previous literatures but an industrially extremely advantageous process for producing N-substituted maleimides which can solve almost all of the major problems of prior art methods.

The constitution and the effect of this invention will be described further in detail below with reference to Comparative Examples and Examples, but this invention is in no way limited to the Examples.

EXAMPLE 1

Into a 1 l reactor equipped with a reflux condenser with a water-separator, a thermometer, a stirrer and a dropping funnel, were placed 68.6 g of maleic anhydride and 300 ml of xylene and the resulting mixture was stirred. Then a mixture of 65.2 g of aniline and 150 ml of xylene was added dropwise from the dropping funnel to the above mixture over a period of about 1 hour. After completion of the dropwise addition, the reaction mixture was heated at 60° C. for 2 hours to complete the reaction. Then, 20 g of a strongly acidic ion exchange resin (Amberlyst ® 15) was added to the reaction mixture, and the whole was heated under reflux at 136 to 140° C. for 16 hours to effect the reaction. During the period 12.5 g of water was separated by means of the water-separator. After completion of the reaction, the ion exchange resin of the catalyst was filtered off and the filtrate was stripped of the solvent under a reduced pressure to yield 109.5 g of yellow crystals. The product was confirmed to be N-phenylmaleimide by its IR spectrum, NMR spectrum and mass spectrum. M.p.: 86-88° C.; yield: 90.3%. No polymeric by-product was formed during the reaction of this Example.

COMPARATIVE EXAMPLE 1

The reaction procedures of Example 1 were repeated except that the catalyst used was altered to 1.2 g of 98% sulfuric acid and the reaction was conducted under reflux (136 to 140° C.) for 16 hours. During the time 10.6 g of water was separated by means of the water-separator.

After completion of the reaction, polymeric by-products were filtered off and then the solvent was distilled off under a reduced pressure. The resulting residue was added dropwise while it was hot (80 to 85° C.) into 2 l of a dilute sodium carbonate solution with vigorous stirring to effect reprecipitation. The precipitate was collected by filtration and dried to give 72.7 g of a yellow solid, m.p. 83 to 86° C., in 60.0% yield. The product gave the same IR spectrum as in Example 1 and was identified as N-phenylmaleimide. The amount of polymeric by-products formed was 38.2 g (31.5% in terms of yield).

EXAMPLE 2

Into the same reaction apparatus as used in Example 1, were placed and stirred 68.6 g of maleic anhydride, 250 ml of xylene, and 50 ml of dimethylformamide to form a solution. A mixture of 65.2 g of aniline and 150 ml of xylene was added dropwise from the dropping funnel to the solution over a period of 1 hour. After completion of the dropwise addition, 20 g of a strongly acidic ion exchange resin (Amberlyst ® 15) was added to the resulting mixture and the whole was heated under reflux at 136 to 140° C. for 3 hours to effect reaction. After completion of the reaction, the ion exchange resin of the catalyst was filtered off and the filtrate was stripped of the solvent under a reduced pressure to give 114.1 g of yellow crystals, m.p. 85–88° C., in 94.1% yield. The product gave the same IR spectrum as in Example 1 and was identified as N-phenylmaleimide. No formation of polymeric by-products was observed at all.

COMPARATIVE EXAMPLE 2

The reaction procedures of Example 2 were repeated except that the catalyst used was altered to 3.6 g of 98% sulfuric acid and the reaction was conducted under reflux (134 to 136° C.) for 2 hours.

After completion of the reaction, polymeric by-products were filtered off and then the solvent was distilled off under a reduced pressure. The resulting residue was redissolved in 400 ml of xylene and the insolubles were filtered off. The filtrate was washed with 100 ml of 1N sodium hydroxide solution to neutralize and remove sulfuric acid of the catalyst. It was further washed twice with 200 ml of water and then the xylene solvent was distilled off to obtain 66.8 g of a yellow solid, m.p. 85°–88° C., in 55.1% yield. The product gave the same IR spectrum as in Example 1 and was identified as N-phenylmaleimide. The amount of polymeric by-products formed was 34.8 g (28.7% in terms of yield).

EXAMPLES 3 TO 5

The reaction procedures of Example 1 were repeated except that 75.1 g of m-toluidine, 89.3 g of p-chloroaniline, or 76.4 g of p-aminophenol was used as the amine to obtain the results shown in Table 1.

TABLE 1

| | Example No. | 3 | 4 | 5 |
|---|---|---|---|---|
| Product | Amine | m-Toluidine | p-Chloroaniline | p-Aminophenol |
| | Maleimide | N—(3-methylphenyl)-maleimide | N—(4-chlorophenyl)-maleimide | N—(4-hydroxyphenyl)-maleimide |
| | Appearance | Yellow solid | Yellow solid | Yellow solid |
| | Amount obtained (g) | 118.7 | 135.7 | 114.9 |
| | Yield (%) | 90.6 | 93.4 | 86.8 |
| | m.p. (°C.) | 35–38 | 108–110 | 187–190 |
| | Polymeric by-product | None | None | None |

EXAMPLES 6 TO 8

The reaction procedures of Example 2 were repeated except that 75.1 g of m-toluidine, 113.4 g of 3,5-dichloroaniline, or 96.7 g of 3-nitroaniline was used as the amine to obtain the results shown in Table 2.

TABLE 2

| | Example No. | 6 | 7 | 8 |
|---|---|---|---|---|
| Product | Amine | m-Toluidine | 3,5-Dichloroaniline | 3-Nitroaniline |
| | Maleimide | N—(3-methylphenyl)-maleimide | N—(3,5-Dichlorophenyl)-maleimide | N—(3-Nitrophenyl)-maleimide |
| | Appearance | Yellow solid | Yellow solid | Yellow solid |
| | Amount obtained (g) | 120.7 | 152.8 | 135.3 |
| | Yield (%) | 92.1 | 90.2 | 88.6 |
| | m.p. (°C.) | 35–38 | 136–138 | 125–128 |
| | Polymeric by-product | None | None | None |

EXAMPLES 9 TO 11

The reaction procedures of Example 2 were repeated except that 20 g of Dowex ® 50WX8, a strongly acidic ion exchange resin, 20 g of Amberlite ® IRC-50, a weakly acidic ion exchange resin, or 20 g o Amberlyst ® A-21, a weakly basic ion exchange resin, was used as the ion exchange resin to obtain the results shown in Table 3.

TABLE 3

| Example No. | 9 | 10 | 11 |
|---|---|---|---|
| Catalyst resin* | Strongly acidic ion exchange resin Dowex ® 50WX8 | Weakly acidic ion exchange resin Amberlite ® IRC-50 | Weakly basic ion exchange resin Amberlyst ® A-21 |
| Refluxing reaction time (hr) | 6 | 8 | 5 |
| Maleimide | N—Phenylmaleimide | N—Phenylmaleimide | N—Phenylmaleimide |
| Appearance | Yellow solid | Yellow solid | Yellow solid |
| Amount obtained (g) | 105.4 | 105.6 | 108.1 |
| Yield (%) | 87.0 | 87.1 | 89.2 |
| Polymeric by-product | None | None | None |

Note:
*Catalyst resin is saturated with water.

EXAMPLES 12 TO 13

The reaction procedures of Examples 2 were repeatd except that 20 g of Amberlite ® IR-120B, a strongly acidic ion exchange resin, of 20 g of Amberlite ® IRA-400, a strongly basic ion exchange resin, was used as the ion exchange resin; toluene was used as the organic hydrocarbon solvent; and the temperature and the time of heating under reflux were altered, to obtain the results shown in Table 4.

TABLE 4

| Example No. | | 12 | 13 |
|---|---|---|---|
| Catalyst resin* | | Strongly acidic ion exchange resin Amberlite ® IR-120B | Strongly basic ion exchange resin Amberlite ® IRA-400 |
| Heating under reflux | Temp. (°C.) | 112 | 110-112 |
| | Time (hr) | 12 | 14 |
| Product | Maleimide | N—Phenyl-maleimide | N—Phenyl-maleimide |
| | Appearance | Yellow solid | Yellow solid |
| | Amount obtained (g) | 106.0 | 93.6 |
| | Yield (%) | 87.4 | 77.2 |
| Polymeric by-product | | None | None |

Note:
*Catalyst resin is saturated with water.

EXAMPLES 14 TO 15

The reaction procedures of Example 2 were repeated except that xylene was used as the aromatic hydrocarbon solvent and further 50 g of dimethylacetamide or 50 g of dimethyl sulfoxide was used as the aprotic polar solvent, to obtain the results shown in Table 5.

TABLE 5

| Example No. | | 14 | 15 |
|---|---|---|---|
| Aprotic polar solvent | | Dimethylacetamide | Dimethyl sulfoxide |
| Product | Appearance | Yellow solid | Yellow solid |
| | Amount obtained (g) | 108.2 | 106.1 |
| | Yield (%) | 89.3 | 87.5 |
| Polymeric by-product | | None | None |

EXAMPLES 16 TO 17

The reaction procedures of Example 2 were repeated except that 51.2 g of n-butylamine or 51.2 g of tert-butylamine was used as the amine, and the reaction time was altered to 3 hours or 15 hours. The liquid product obtained was purified and isolated by distillation under a reduced pressure. The results obtained are shown in Table 6.

TABLE 6

| Example No. | | 16 | 17 |
|---|---|---|---|
| Amine | | n-Butylamine | tert-Butylamine |
| Reaction time (hr) | | 3 | 15 |
| Product | Maleimide | N—(n-Butyl)-maleimide | N—(tert-Butyl)-maleimide |
| | Appearance | Colorless transparent liquid | Colorless transparent liquid |
| | Amount obtained (g) | 82.6 | 60.3 |
| | Yield (%) | 77.0 | 56.2 |
| | B.p. | 86-89 | 62-64 |

TABLE 6-continued

| Example No. | 16 | 17 |
|---|---|---|
| (°C./6 mmHg) | | |

We claim:

1. A process for producing N-substituted maleimides which comprises heating maleic anhydride and an aromatic or aliphatic primary amine in the presence of an ion exchange resin in an organic solvent in the temperature range of 50° C. to 160° C. to effect cyclodehydration.

2. A process according to claim 1, wherein the aromatic primary amine is aniline, naphthylamine, toluidine, dimethylaniline, chloroaniline, dichloroaniline, hydroxyaniline, nitroaniline or phenylenediamine.

3. A process according to claim 1, wherein the aliphatic primary amine is methylamine, ethylamine, propylamine, butylamine, benzylamine, cyclohexylamine or ethylenediamine.

4. A process according to claim 1, wherein the ion exchange resin is a strongly acidic ion exchange resin, a weakly acidic ion exchange resin, or a weakly basic ion exchange resin.

5. A process according to claim 1, wherein the organic solvent is an aromatic hydrocarbon solvent.

6. A process according to claim 1, wherein the organic solvent is a mixture of an aromatic hydrocarbon solvent and an aprotic polar solvent.

7. A process for producing N-substituted maleimides which comprises heating aromatic or aliphatic monoamides of maleic acid in the presence of an ion exchange resin in an organic solvent in the temperature range of 50° C. to 160° C. to effect cyclodehydration.

8. A process according to claim 7, wherein the aromatic or aliphatic monoamides of maleic acid is a product formed by the reaction of maleic anhydride with a corresponding amine, said monoamides being used without being separated from the reaction mixture.

9. A process according to claim 7, wherein the aromatic primary amine is aniline, naphthylamine, toluidine, dimethylaniline, chloroaniline, dichloroaniline, hydroxyaniline, nitroaniline, or phenylenediamine.

10. A process according to claim 7, wherein the aliphatic primary amine is methylamine, ethylamine, propylamine, butylamine, benzylamine, cyclohexylamine, or ethylenediamine.

11. A process according to claim 7, wherein the ion exchange resin is a strongly acidic ion exchange resin, a weakly acidic ion exchange resin, or a weakly basic ion exchange resin.

12. A process according to claim 7, wherein the organic solvent is an aromatic hydrocarbon solvent.

13. A process according to claim 7, wherein the organic solvent is a mixture of an aromatic hydrocarbon solvent and an aprotic polar solvent.

14. A process according to claim 1 wherein said ion exchange resin is present in an amount from 1 to 40% by weight based on the amount of the reaction liquid.

* * * * *